United States Patent
Kessler et al.

(10) Patent No.: US 9,414,992 B2
(45) Date of Patent: *Aug. 16, 2016

(54) PROCESS FOR PRODUCING A SOLID DISPERSION OF AN ACTIVE INGREDIENT

(71) Applicant: Abbott GmbH & Co. KG, Weisbaden (DE)

(72) Inventors: Thomas Kessler, Schifferstadt (DE); Jörg Breitenbach, Mannheim (DE); Christoph Schmidt, Mannheim (DE); Matthias Degenhardt, Ludwigshafen (DE); Jörg Rosenberg, Ellerstadt (DE); Harald Krull, Ludwigshafen (DE); Gunther Berndl, Herxheim am Berg (DE)

(73) Assignee: Abbvie Deutschland GmbH & CO KG, Wiesbaden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/094,533

(22) Filed: Dec. 2, 2013

(65) Prior Publication Data
US 2014/0087060 A1    Mar. 27, 2014

Related U.S. Application Data

(63) Continuation of application No. 12/279,385, filed as application No. PCT/EP2007/052315 on Mar. 12, 2007, now abandoned.

(60) Provisional application No. 60/781,398, filed on Mar. 10, 2006.

(30) Foreign Application Priority Data

Mar. 10, 2006  (EP) ..................................... 06004999

(51) Int. Cl.
*A61K 9/20*    (2006.01)
*A61K 47/32*   (2006.01)
(Continued)

(52) U.S. Cl.
CPC ................ *A61J 3/00* (2013.01); *A61K 9/2095* (2013.01); *A61K 9/2893* (2013.01); *A61K 47/32* (2013.01);
(Continued)

(58) Field of Classification Search
CPC ........ B29C 47/38; B29C 47/60; B29C 47/64; B29C 47/402; B29C 47/0004; B29C 47/404; B29C 47/82; B29C 47/76; B29C 47/0871; B29C 47/1063; B29C 47/1045; B29C 47/0825; B29C 47/6012; B29C 47/6031; B29C 47/6043; B29C 47/6087; B29C 47/6056; B29C 47/40; B29C 35/02; B29K 2105/0005; B29K 2105/0035; B29K 2105/0038; B29K 2105/0064
USPC ..................................................... 264/211.23
See application file for complete search history.

(56) References Cited

U.S. PATENT DOCUMENTS 4,801,460 A  1/1989  Goertz et al.
4,880,585 A  11/1989  Klimesch et al.
(Continued)

FOREIGN PATENT DOCUMENTS

DE  197 21 467 A1  11/1998
DE  10338180 B3   4/2005
(Continued)

OTHER PUBLICATIONS

Martin, Charles; Pharmaceutical Extrusion Technology; Ghebre Selassie & Martin (eds.), Informa Health Care 2007.
(Continued)

*Primary Examiner* — Yogendra Gupta
*Assistant Examiner* — Emmanuel S Luk
(74) *Attorney, Agent, or Firm* — Saul Ewing LLP; Peter C. Lauro, Esq.

(57) ABSTRACT

A process for producing a solid dispersion of an active ingredient which comprises feeding the active ingredient and a matrix-forming agent to an extruder and forming a uniform extrudate, wherein the extruder comprises at least two rotating shafts (2), each of the shafts (2) carrying a plurality of processing elements disposed axially one behind the other, the processing elements defining (i) a feeding and conveying section (R; A), (ii) at least one reverse-flight section (D), and (iii) a discharging section (E), wherein the processing elements defining the reverse-flight section (R; D) comprise at least one reverse-flight element (14) which is based on a screw-type element having a conveying direction being opposite to the general conveying direction of the extruder.

28 Claims, 7 Drawing Sheets

(51) Int. Cl.

| | | |
|---|---|---|
| *A61K 9/28* | (2006.01) | |
| *B01F 7/00* | (2006.01) | |
| *A61J 3/00* | (2006.01) | |
| *B29C 47/00* | (2006.01) | |
| *B29C 47/38* | (2006.01) | |
| *B29C 47/60* | (2006.01) | |
| *B29C 47/62* | (2006.01) | |
| *B29C 47/64* | (2006.01) | |
| *B29C 47/86* | (2006.01) | |
| B29C 35/02 | (2006.01) | |
| B29C 47/08 | (2006.01) | |
| B29C 47/10 | (2006.01) | |
| B29C 47/40 | (2006.01) | |
| B29C 47/76 | (2006.01) | |
| B29C 47/82 | (2006.01) | |
| B29K 105/00 | (2006.01) | |
| B29K 105/16 | (2006.01) | |

(52) U.S. Cl.
CPC ........... *B01F 7/0045* (2013.01); *B29C 47/0004* (2013.01); *B29C 47/38* (2013.01); *B29C 47/402* (2013.01); *B29C 47/60* (2013.01); *B29C 47/6012* (2013.01); *B29C 47/6031* (2013.01); *B29C 47/6037* (2013.01); *B29C 47/6043* (2013.01); *B29C 47/6056* (2013.01); *B29C 47/6087* (2013.01); *B29C 47/625* (2013.01); *B29C 47/64* (2013.01); *B29C 47/827* (2013.01); *B29C 47/862* (2013.01); *A61K 9/2027* (2013.01); *B29C 35/02* (2013.01); *B29C 47/0009* (2013.01); *B29C 47/0825* (2013.01); *B29C 47/0871* (2013.01); *B29C 47/1045* (2013.01); *B29C 47/1063* (2013.01); *B29C 47/40* (2013.01); *B29C 47/404* (2013.01); *B29C 47/76* (2013.01); *B29C 47/82* (2013.01); *B29K 2105/0005* (2013.01); *B29K 2105/0035* (2013.01); *B29K 2105/0038* (2013.01); *B29K 2105/0064* (2013.01); *B29K 2105/16* (2013.01)

(56) References Cited

U.S. PATENT DOCUMENTS

| | | | |
|---|---|---|---|
| 4,957,681 A | | 9/1990 | Klimesch et al. |
| 5,075,291 A | * | 12/1991 | DuRoss .......................... 514/60 |
| 5,266,256 A | * | 11/1993 | Jerman .................... B01J 19/20 264/211.24 |
| 5,318,358 A | | 6/1994 | Wobbe et al. |
| 5,456,923 A | | 10/1995 | Nakamichi et al. |
| 5,472,733 A | * | 12/1995 | Degady ................ A23G 3/0215 426/448 |
| 5,549,920 A | | 8/1996 | Choudhury |
| 5,641,516 A | * | 6/1997 | Grabowski et al. ............ 424/489 |
| 5,684,040 A | * | 11/1997 | Grabowski et al. ............ 514/457 |
| 6,106,142 A | | 8/2000 | Rockstedt |
| 6,221,368 B1 | | 4/2001 | Breitenbach et al. |
| 6,318,650 B1 | | 11/2001 | Breitenbach et al. |
| 6,365,188 B1 | | 4/2002 | Baert et al. |
| 6,499,984 B1 | | 12/2002 | Ghebre-Sellassie et al. |
| 6,569,455 B1 | * | 5/2003 | Kanikanti et al. ............. 424/464 |
| 7,270,471 B2 | | 9/2007 | Blach |
| 2002/0044968 A1 | | 4/2002 | van Lengerich |
| 2003/0077297 A1 | * | 4/2003 | Chen et al. ..................... 424/400 |
| 2004/0131725 A1 | | 7/2004 | Song et al. |
| 2004/0219220 A1 | * | 11/2004 | Sherry et al. .................. 424/489 |
| 2005/0024986 A1 | | 2/2005 | Mattingly |
| 2006/0193896 A1 | * | 8/2006 | Boghani ............... A23L 1/0029 424/439 |
| 2006/0293457 A1 | | 12/2006 | Nadella et al. |
| 2014/0087060 A1 | | 3/2014 | Kessler et al. |

FOREIGN PATENT DOCUMENTS

| | | |
|---|---|---|
| EP | 0 240 904 A2 | 10/1987 |
| EP | 0 240 906 A2 | 10/1987 |
| EP | 0 337 256 A2 | 10/1989 |
| EP | 0 580 860 A1 | 2/1994 |
| EP | 1 685 942 A | 8/2006 |
| JP | 2000-502300 A | 2/2000 |
| JP | 2001-527464 A | 12/2001 |
| JP | 2003-011193 A | 1/2003 |
| JP | 2005-533681 A | 11/2005 |
| JP | 2011-501050 A | 1/2011 |
| KR | 10-2000-0036066 | 6/2000 |
| WO | 9218106 A1 | 4/1992 |
| WO | 96/03978 A1 | 2/1996 |
| WO | 98/18610 A | 5/1998 |
| WO | 98/18610 A1 | 6/1998 |
| WO | 01/34687 A | 5/2001 |
| WO | 01/89679 A | 11/2001 |
| WO | 03077827 A1 | 3/2003 |
| WO | 03/077827 A | 9/2003 |
| WO | 2006/024881 A | 3/2006 |
| WO | 20060244881 A2 | 3/2006 |
| WO | 2007/104748 A2 | 9/2007 |

OTHER PUBLICATIONS

Breitenbach, Jorg; Melt Extrusion; from process to drug delivery technology; European Journal of Pharmaceutics and Biopharmaceutics 54 (2002) 107-117.
Experimental Report-Extrusion of paracetamol based on the teaching of WO 2007/104747 A2; Oppo./EP 1 996 163 (D7471) Enclosure O11.
Wildi, Robert H., et al., Understanding Compounding; Hanser Publishers, Munich 1988; OPpo./EP 1 996 163 (D7471) Enclosure O8.
Crowley, Michael M., et al.; Pharmaceutical Applications of Hot-Melt Extrusion: Part I; Drug Development and Industrial Pharmacy, 33:909-926, 2007.
Suneetha, A., et al.; A Validated RP HPLC Method for Simultaneous Estimation of Lopinavir and Ritonavir in Combined Dosage Form; International Journal of Pharmacy and Pharmaceutical Sciences; vol. 3, Issue 1, 2011, pp. 49-51.
Twin Screw Extrusion: Technology and Principles, White, Carl Hanser GmbH & Co. KG (1st ed.) pp. 209-210 (1991).
Rauwendaal, Chris; Polymer Extrusion; Oppo./EP 1 996 163 (D7471); Enclosure O12, pp. 522-533 (1991).
Form PCT/ISA/210 issued in PCT/EP2007/052315(ISR), Abbott GmbH, Jun. 28, 2007.
Form PCT/ISA/237 issued in PCT/EP2007/052315 (Written Opinion), Abbott GmbH, Jun. 28, 2007.
Form PCT/ISA/210, ISR, issued in PCT/EP2007/052314, Oct. 12, 2007.
Form PCT/ISA/237, Written Opinion, issued in PCT/EP2007/052314, Oct. 12, 2007.
English translation of Japanese Office Action (Official Notification of Reason for Rejection) dated Sep. 10, 2013, Japanese Patent Application No. 2008-557771.
Potente et al., Intern Polymer Processing IX, Hanser 1994, 11-25.
Expert Declaration of Prof. Dr. Klaus-JürgenSteffens May 18, 2015.
Sources, Quality and Prices of Active Pharmaceutical Ingredients of Antiretroviral Drugs—Results of a 2010 WHO Survey.
C. Hanser Vertag, Experimental Report Extrusion of lopinavir/ntonavir combinations based on the teaching of WO 2007/104747 A2 1986.
European Pharmacopoeia entry "Ritonavir" World Health Organization. Oct. 2013. Retrieved Apr. 22, 2014 —.
Grounds for Appeal, EPO Form 3344, Dec. 3, 2015.
Experimental Report Extrusion of lopinavir/ritonavir combinations based on the teaching of WO 2007/104747 A2 (Enclousre O17).
Summary of Data (Eclosure O18).
2d Expert Declaration of Prof. Dr. Stettens with CV and Publication (Ergänzende Gutachterliche Stellungnahme im Einspruchsverfahren betreffend EP 1 996 163 B1), Nov. 17, 2015 (Enclosure O19).

* cited by examiner

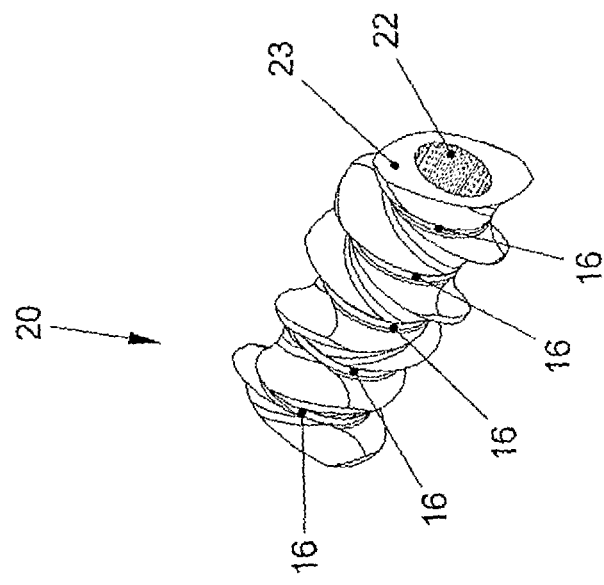
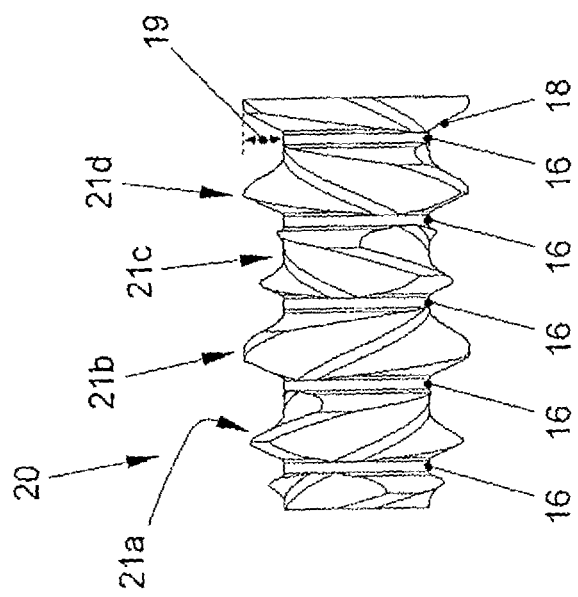
FIG. 6A
FIG. 6B

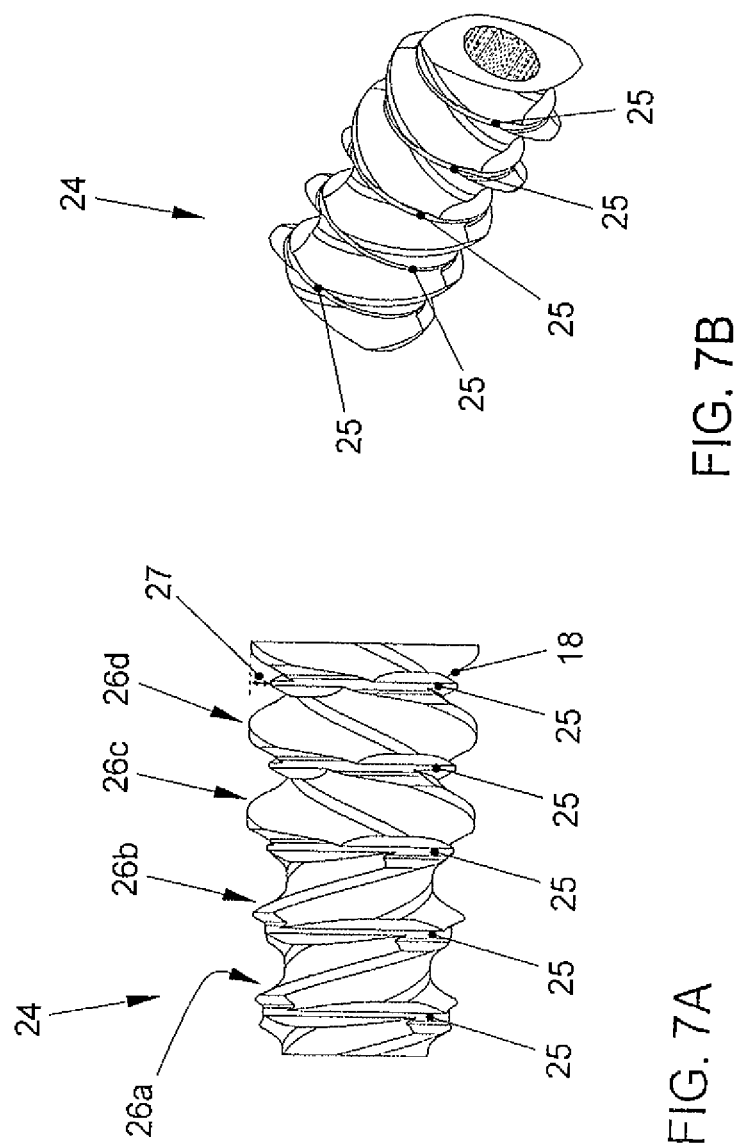

PROCESS FOR PRODUCING A SOLID DISPERSION OF AN ACTIVE INGREDIENT

RELATED APPLICATION DATA

This application is a continuation of U.S. application Ser. No. 12/279,385, which is the U.S. national phase under 35 U.S.C. §371 of International application Ser. No. PCT/EP2007/052315, filed Mar. 12, 2007, designating the United States and published in English as publication No. WO 2007/104748 A2 on Sep. 20, 2007 and claiming priority to European patent application Ser. No. 06004999.6, filed Mar. 10, 2006, and U.S. provisional application Ser. No. 60/781,398, filed Mar. 10, 2006. The entire disclosures of each of the aforementioned patent applications are incorporated herein by this reference.

BACKGROUND OF THE INVENTION

The present invention relates to a process for producing a solid dispersion of an active ingredient which comprises feeding the active ingredient and a matrix-forming agent to an extruder and forming a uniform extrudate.

A continuous process for producing solid pharmaceutical forms, including solid solution products, has been known for some time and entails converting a melt of polymeric binder which contains active ingredients into the required drug form by injection molding or extrusion and subsequent shaping (see, for example, EP-A-240 904, EP-A-240 906 and EP-A-337 256). Satisfactory results are obtained in this process when the active ingredient has a low melting point and/or a high solubility in the molten polymeric binder. Active ingredients having a low melting point are liquefied upon contact with the polymeric binder melt, and the liquefied active ingredient can be readily dispersed in the polymeric binder melt. Alternatively, active ingredients having a high solubility in the molten polymeric binder readily dissolve in the polymeric binder melt.

Problems occur when the active ingredient has a high melting point and/or a limited solubility in the molten polymeric binder. Adequate dispersion of the active ingredient may require high temperatures of the extruder barrel, a relatively long mixing time and/or high shear in order to bring about sufficient mixing of the active ingredient with the polymeric binder melt. This may result in local overheating and damage to the product, especially when a shear- and temperature-sensitive active ingredient is being used. A further disadvantage of the necessity of high temperatures of the extruder barrel is high energy costs.

Furthermore, EP 0 580 860 B2 describes a process for producing a solid dispersion of a drug dissolved in a polymer, wherein a twin-screw extruder equipped with paddle means or kneading blocks is employed. Such kneading blocks consist of, e.g. disk cams disposed offset in the manner of a spiral staircase. The substance is pressed through a narrow tapered gap between the disk cams and the extruder housing. During the passage through the extruder, the material is thus subjected to high local shear forces, which may lead to excessive degradation of the active ingredient and/or the polymer. Shearing may also cause excessive wear of the extrusion equipment.

SUMMARY OF THE INVENTION

It is an object of the present invention to provide a process for producing a solid dispersion of an active ingredient in a matrix-forming agent, in particular in a polymer, with improved mixing and homogenization abilities. Furthermore, high temperatures or high local shear forces should be avoided.

It is another object of the present invention to provide a process for producing a solid dispersion of an active ingredient in a matrix-forming agent, in particular in a polymer, in which degradation of the active ingredient and/or the matrix-forming agent and/or ancillary substances is minimized.

BRIEF DESCRIPTION OF THE DRAWINGS

FIG. 6A and FIG. 6B show another preferred embodiment of a mixing element in accordance with the present invention; and FIG. 7A and FIG. 7B show another preferred embodiment of a mixing element in accordance with the present invention.

DETAILED DESCRIPTION OF THE INVENTION

Figure 1:
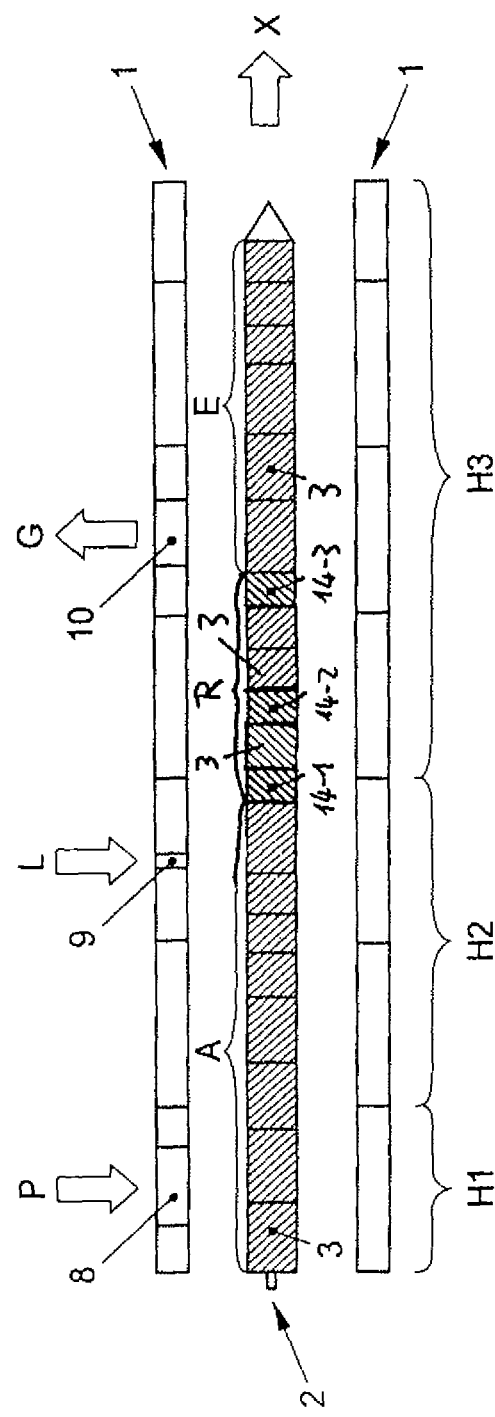
FIG. 1 shows schematically a sectional view of the extruder that was used for an example in accordance with the process according to the present invention.

The present invention provides a process for producing a solid dispersion of an active ingredient which comprises feeding the active ingredient and a matrix-forming agent to an extruder and forming a uniform extrudate. The extruder comprises at least two rotating shafts, each of the shafts carrying a plurality of processing elements disposed axially one behind the other. The processing elements define (i) a feeding and conveying section, (ii) at least one reverse-flight section, and (iii) a discharging section. The feeding and conveying section is positioned farthest upstream, close to the hopper of the extruder, the at least one reverse-flight section is positioned downstream of the feeding and conveying section, and the discharging section is positioned farthest downstream, close to the discharge opening of the extruder. The term "downstream" as used herein, refers to direction in which the material is being conveyed in the extruder.

The processing elements may be formed separately. They may be strung, one behind the other, along the shaft of the extruder. However, it may also be possible that the processing elements are formed integrally. In this case, the surface structure of the element forms said processing elements.

According to the invention, the processing elements defining the reverse-flight section comprise at least one reverse-flight element which is based on a screw-type element having a conveying direction opposite to the general conveying direction of the extruder. "A reverse-flight element which is based on a screw-type element" is intended to mean an element whose basic shape is that of a screw element. Such an element differs from conventionally known kneading elements or modified kneading elements. In particular, a kneading element allows an enhanced flow of the extrudate between its periphery ridges (i.e., its outer edge) and the barrel or bore of the extruder. A reverse-flight element which is based on a screw-type element according to the invention does only allow a small amount of the extrudate to flow between the edge of the screw and the barrel or bore of the extruder. In an example of a conventional kneading element the clearings between the end of the element closest to the surface of the bore is greater than the clearance between the end of the reverse-flight elements according to the present invention closest to the surface of the bore.

The at least one reverse-flight element has a screw with a reverse-flight relative to the screw-type elements which may be arranged in the feeding and conveying section which define the general conveying direction of the extruder.

Furthermore, the reverse-flight element may preferably not have a plane surface area with a normal parallel and opposite to the general conveying direction. In particular, the reverse-flight element may have no face that is perpendicular to the general conveying direction. Therefore, it differs from kneading elements also with respect to the orientation of the surfaces. Moreover, the reverse-flight element does not have abutting faces that are perpendicular to the general conveying direction.

The reverse-flight element serves to create sufficient back-pressure to allow for a desired degree of mixing and/or homogenization. It is designed to stow the material conveyed in the extruder. Therefore it may also be called a back-pressure element. The reverse-flight element may be derived from a reverse-flight screw, such that they convey the material in an opposite direction relative to the general conveying direction of the extruder. The reverse-flight elements may be formed separately from other processing elements or integrally with other processing elements.

Surprisingly, it has been found that the at least one reverse-flight element enable a sufficient degree of mixing or homogenization. Furthermore, a relatively low temperature of the barrel of the extruder may be chosen without deteriorating the quality of the extrudate.

According to an embodiment, the processing elements defining a reverse-flight section comprise at least two reverse-flight elements and at least one positive-flight screw-type element which is arranged between said two reverse-flight elements. In particular, the screw pitch of the reverse-flight elements is in a range from −0.5 times to −1.5 times, preferably from −0.8 times to −1.2 times, the screw-pitch of the screw-type elements of the feeding and conveying section and/or the screw-type element(s) arranged between the two reverse-flight elements. Preferably, the screw-pitch of the reverse-flight elements is the same as the screw pitch of the screw-type elements of the feeding and conveying section and/or the screw-type element(s) arranged between the two reverse-flight elements. Therefore, the difference between the screw-type elements and the reverse-flight elements may only be the direction of rotation of the screw.

The screw-type element(s) arranged between the two reverse-flight elements and the screw-type elements of the feeding and conveying section may be different. However, preferably, they are identical. The reverse-flight elements may be identical to the screw-type elements not only with respect to the absolute value of the screw pitch, but also with respect to the geometries of the surfaces that come into contact with the extrudate.

According to an embodiment, the processing elements defining a reverse-flight section comprise at least three reverse-flight elements, wherein at least one positive-flight screw-type element is arranged between the respective successive reverse-flight elements. Therefore, in the reverse-flight section, a reverse-flight element is followed by one at least one positive-flight screw-type element which is followed by a reverse-flight element which is again followed by at least one positive-flight screw-type element which is followed by the third reverse-flight element. The length of the positive-flight screw-type element(s) arranged between the second and third reverse-flight elements is in a range from 1 to 15 times, preferably from 1.5 times to 5 times, the length of the positive-flight screw-type element(s) arranged between the first and second reverse-flight elements. Preferably, the length of the positive-flight screw-type element(s) arranged between the second and third reverse-flight elements is twice that of the positive-flight screw-type element(s) arranged between the second and third reverse-flight elements.

According to another embodiment, the processing elements defining the reverse-flight section comprise at least four reverse-flight elements, wherein at least one positive-flight screw-type element is arranged between the respective successive reverse-flight elements, and wherein the length of the positive-flight element(s) arranged between successive reverse-flight elements is the same.

In preferred embodiments, the processing elements additionally comprise at least one mixing element that is derived from a screw-type element. This at least one mixing element is arranged in the reverse-flight section. The reverse-flight section comprising such a mixing element may therefore also be called a mixing section. The mixing element(s) has/have preferably recesses formed in the screw flight of the screw-type element.

A mixing element "being derived from a screw type element" is intended to mean an element whose basic shape is that of a screw element, but which has been modified such that it exerts a compounding or mixing effect in addition to a conveying effect. The underlying screw type element may have a positive-flight (positive-feed, "right-handed") screw element, may have a reverse-flight (negative-feed, "left-handed") screw element or a combination thereof. It is believed that the mode of mixing exerted by the mixing elements is predominantly distributive rather than dispersive mixing.

Until now, paddle means or kneading blocks have conventionally been employed in kneading and plasticizing pharmaceutical mixtures. These kneading blocks consist of cam disks mutually offset at an angle in a peripheral direction. The cam disks have abutting faces that are perpendicular to the general conveying direction in the extruder. Whereas these kneading blocks provide effective kneading and homogenization, high local shear occurs at the edges of the cam disks. This local shear is believed to be detrimental to the active ingredient or other components.

The mixing elements used in accordance with the invention do not have abutting faces that are perpendicular to the general conveying direction.

Preferred mixing elements do not have a plane surface area with a normal parallel and opposite to the general conveying direction. In particular, the mixing elements may have no face that is perpendicular to the general conveying direction. Therefore, they differ from kneading elements with respect to the orientation of the surfaces. However, mixing elements may allow an enhanced flow of the extrudate between their periphery ridge (i.e., their outer edge) and/or said recesses and the barrel or bore of the extruder.

Typically, the mixing element used in accordance with the invention has recesses formed in the screw flight of a screw type element. Mixing elements of this type are known as such and, for example, described in WO 2004/009326 A1, U.S. Pat. No. 5,318,358 and U.S. Pat. No. 6,106,142.

A preferred mixing element has a plurality of concentric ring portions formed by grooves turned into a screw type element. Therefore, the mixing element has a continuous screw flight, which is interrupted only by turned grooves with ring portions.

Surprisingly, it has been found that these mixing elements enable a sufficient degree of mixing or homogenization with less degradation of the active ingredient or formation of other ingredients, compared to a conventional process employing paddle means or kneading blocks. Furthermore, a lower temperature of the barrel of the extruder may be chosen while still obtaining an extrudate of the same quality. Additionally, it has been found, surprisingly, that the inventive mixing elements provide a better self-cleaning effect. This self-cleaning effect prevents that residues of the extruded material remain within the extruder over extended periods of time.

The extruder comprises at least two axis-parallel shafts and, in preferred embodiments, is a twin-screw extruder. The shafts may be co-rotating or counter-rotating, but are preferably co-rotating. The extruder may comprise more than two and, e.g., up to six shafts. Processing elements disposed on adjacent shafts closely intermesh.

The feeding and conveying section as well as the discharging section allow for a smooth passage of the material fed to the extruder from the feed end to the discharge end of the extruder. The processing elements employed in the feeding and conveying section or the discharging section are typically in the form of an endless screw element, i. e. an element characterized by an essentially continuous screw flight.

According to an advantageous aspect of the invention, the processing elements define [0029] (i) a feeding and conveying section, [0030] (ii) a first mixing section, positioned downstream of the feeding and conveying section, and [0031] (iii) an intermediate conveying section, positioned downstream of the first mixing section, [0032] (iv) a reverse-flight section (second mixing section), positioned downstream of the intermediate conveying section, and [0033] (v) a discharging section, wherein the processing elements defining the first mixing section comprise at least one mixing element and the processing elements defining the reverse-flight section comprise at least one mixing element and downstream thereto at least one reverse-flight element.

The length of the feeding and conveying section is suitably selected such that the material which is fed into the extruder has undergone significant softening or is nearly melting when the material enters the first mixing section or reverse-flight section if no mixing section is arranged upstream the reverse-flight section. Preferably, the feeding and conveying section corresponds to from about 20 to about 40% of the entire length of the shaft. Preferably, the discharging section corresponds to from about 15 to about 30% of the entire length of the shaft.

In accordance with an advantageous aspect of the invention, a twin-screw extruder is used. It has at least two parallel co-rotating shafts. In the mixing section or in the mixing sections the shafts are equipped with intermeshing mixing elements. The face of the mixing elements is limited by circular arcs corresponding to the outside screw diameter, the screw core diameter and at most the centre distance of the mixing elements. The shafts are guided on circular segments of the extruder housing that are parallel to the shafts.

Advantageously, the mixing element comprises screw portions between the ring portions which first cause a pressure buildup that forces the substance through the annular gap between the extruder housing and the ring portions with shearing action and elongation; the pressure is then reduced again. The recurring sequence of shear gap passage, pressure buildup, shear gap passage, etc., on the mixing elements causes a defined stress on the substance and thus a uniform stress, without unduly stressing in particular the active ingredient.

The screw portions between the ring portions of a mixing element may have the same pitch flight. However, the pitch flight of these screw portions may also be different. According to an advantageous embodiment of the present invention, the screw portions of at least one mixing element on each shaft have partly a positive screw flight and partly a reverse-screw flight.

The annular and/or shear gap between the ring portions and the concave circular segments of the extruder housing can have a different height to produce a sufficient mixing effect for the active ingredient in the matrix-forming agent. For this purpose the ring portion might correspond only to the core diameter of the screw shaft. The annular gap may also have a height of from 10 percent to 90 percent of the flight depth of the screw. Furthermore, the diameter of the ring portions may correspond approximately to the center distance of two adjacent shafts.

Before the substance is stressed during its passage through the annular or shear gap, it must be transported a certain conveying distance by a screw portion to build up the required pressure. For this purpose the screw portions located between two adjacent ring portions generally have a length of at least $1/10$, preferably at least $1/5$, of the screw diameter. The turned grooves of the ring portions preferably have a depth of, for example, $1/2$ or less of the flight depth. The angle of the flanks of the turned grooves can be, for example, 30 to 90 degrees. Preferably, oblique grooves are turned, in particular at an angle of about 60 degrees, to the shaft axis.

By stock removal on the screw crest and flanks, the mixing element can be provided with further portions. Thus, in particular a mixing section with substantially neutral conveying action can be provided by stock removal.

After the annular gaps the screw flight can continue at the same pitch angle. That is, the screw portions of the mixing element can form a continuous screw flight apart from the turned interruptions in the area of the ring portions.

The ring portions permit additional dispersing surfaces to be gained. A substantial enlargement of the dispersing surface can moreover be obtained if the screw portions between the ring portions are disposed at a progressive angular offset from each other with the same direction of rotation, for example, at an angular offset by half the flight angle. The angularly offset screw portions form faces angularly offset in step-like fashion as additional dispersing surfaces.

Figure 2:
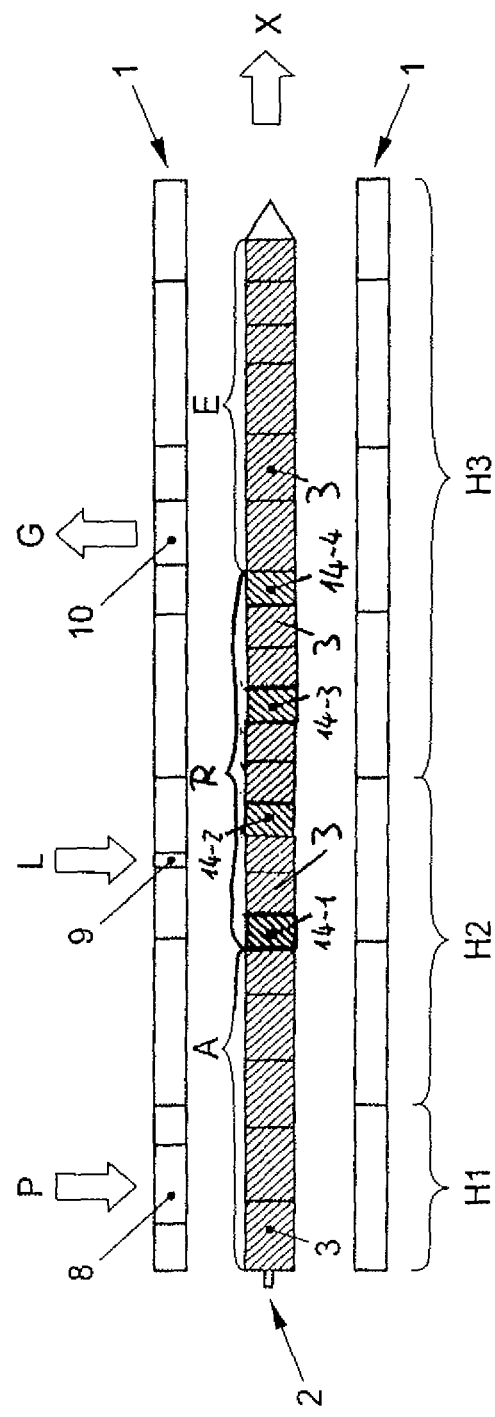
FIG. 2 shows schematically a sectional view of an example of an extruder for an embodiment of the process according to the present invention.

According to one embodiment of the invention the mixing element or the mixing elements used on the shafts of the twin-screw extruder are described in WO 2004/009326 A1, which is incorporated herein by reference. FIGS. 2 and 5 of WO 2004/009326 A1 show preferred mixing elements used in accordance with the invention. Further examples are described below with reference to the accompanied drawings.

The solid dispersions manufactured by the process of the present invention contain one or more active ingredient and, optionally, additives. Additives may be used to impart desirable properties to the solid dispersions or to facilitate the manufacture thereof. Although the actives and additives may be incorporated into the extruded mixture at any appropriate stage of the process, it may be preferred to introduce a part or all of the active ingredients or additives into the extruder separately from the matrix-forming agent and/or other components.

Therefore, in an embodiment of the inventive process, at least part of the matrix-forming agent is fed to the hopper of the extruder and at least one component selected from [0046]

(i) the remainder of the matrix-forming agent, [0047] (ii) an active ingredient, [0048] (iii) an additive, and [0049] (iv) combinations thereof, is introduced into the extruder through an opening in the extruder barrel at a position upstream of or in a mixing section, or the reverse-flight section.

Preferably, the at least one component is introduced into the extruder at a position at or close to the junction of the feeding and conveying section and a mixing section or the reverse-flight section. The component may be solid, e.g. powdered, but preferably is liquid or liquefied.

Most preferably, the at least one component comprises a pharmaceutically acceptable surfactant.

The substances which are fed to the extruder are melted in order to homogenize the melt and to disperse or dissolve the active ingredient in the polymer efficiently.

"Melting" means transition into a liquid or rubbery state in which it is possible for one component to be homogeneously embedded in the other. Melting usually involves heating above the softening point of the polymer. Usually, the maximum melt temperature is in the range of 70 to 250° C., preferably 80 to 180° C., most preferably 100 to 140° C.

The extruder housing is heated in order to form a melt from the substances fed to the extruder. It will be appreciated that the working temperatures will also be determined by the kind of extruder or the kind of configuration within the extruder that is used. A part of the energy needed to melt, mix and dissolve the components in the extruder can be provided by heating elements, while the friction and shearing of the material in the extruder can also provide the mixture with a substantial amount of energy and aid in the formation of a homogeneous melt of the components.

In order to obtain a homogeneous distribution and a sufficient degree of dispersion of the active ingredient, the active ingredient-containing melt is kept in the heated barrel of the melt extruder for a sufficient length of time.

According to a further aspect of the invention, the extruder barrel comprises several heating zones. Preferably, the portion of the barrel upstream of the first mixing element or first reverse-flight element is maintained at a lower temperature than the portion of the barrel downstream of the first mixing element or the first reverse-flight element. It has been found that this temperature distribution leads to a homogeneous, smooth and transparent extrudate which, in particular, has not been damaged by temperatures too high for the active ingredient.

In the extrudates produced according to the present invention, one or more active ingredients are dispersed evenly throughout the polymer. This encompasses systems having small particles, typically of less than 1 .mu.m in diameter, of active ingredient in the polymer phase. These systems do not contain any significant amounts of active ingredients in their crystalline or microcrystalline state, as evidenced by thermal analysis (DSC) or X-ray diffraction analysis (WAXS). Typically, at least 98% by weight of the total amount of active ingredients is present in an amorphous state.

When the extrudate is chemically and physically uniform or homogenous throughout or consists of one phase (as defined by thermodynamics), the dispersion is called a "solid solution". Solid solutions of active ingredients are preferred physical systems.

The polymer does not contain significant amounts of volatile solvents. The term "volatile solvent" is intended to encompass water and any compound that is liquid at ambient temperature and has a higher volatility than water. Typically, the matrix contains less than 25%, preferably less than 6%, and most preferably less than 3% by weight of a volatile solvent.

Preferred extrudates formed by the process according to the invention comprise: [0061] from about 8 to 99.9% by weight (preferably 40 to 85% by weight, most preferably 50 to 70% by weight) of the matrix-forming agent (or any combination of such matrix-forming agents), [0062] from about 0.1 to 49% by weight (preferably 1 to 30% by weight) of an active ingredient or a combination of active ingredients, [0063] from 0 to 25% by weight (preferably 2 to 15% by weight) of at least one pharmaceutically acceptable surfactant, and [0064] from 0 to 25% by weight (preferably 0 to 15% by weight) of additives.

The matrix-forming agent may be any agent capable of setting or gelling from a liquified state, e. g. from a molten state, to form a continuous matrix. Mixtures of matrix-forming agents can, of course, be used.

Useful matrix-forming agents are selected from polyols (i.e. sugar alcohols, sugar alcohol derivatives, or maltodextrines), waxes and lipids.

Suitable sugar alcohols include mannitol, sorbitol, xylitol; sugar alcohol derivatives include isomalt, or hydrogenated condensed palatinose (as described in DE-A 10262005); further matrix-forming agents are maltodextrines.

Preferably, the matrix-forming agent includes a pharmaceutically acceptable polymer or a mixture of pharmaceutically acceptable polymers. Usually, pharmaceutically acceptable polymers are water-soluble or at least water-dispersible.

Generally, the pharmaceutically acceptable polymer employed in the invention has a Tg of at least about +10° C., preferably at least about +25° C., most preferably from about 40.degree. to 180° C. "Tg" means glass transition temperature. Methods for determining the Tg values of organic polymers are described in "Introduction to Physical Polymer Science", 2nd Edition by L. H. Sperling, published by John Wiley & Sons, Inc., 1992. The Tg value can be calculated as the weighted sum of the Tg values for homopolymers derived from each of the individual monomers i that make up the polymer, i.e. Tg=.SIGMA.W.sub.i X.sub.i where W is the weight percent of monomer i in the organic polymer and X is the Tg value for the homopolymer derived from monomer i. Tg values for the homopolymers are indicated in "Polymer Handbook", 2nd Edition by J. Brandrup and E. H. Immergut, Editors, published by John Wiley & Sons, Inc., 1975.

Pharmaceutically acceptable polymers having a Tg as defined above allow the preparation of solid dispersions that are mechanically stable and, within ordinary temperature ranges, sufficiently temperature stable so that said solid dispersions may be used as dosage forms without further processing or can be compacted to tablets with only a small amount of tabletting aids. Dosage forms are, e. g., tablets, capsules, implants, films, foams, suppositories.

The pharmaceutically acceptable polymer comprised in the composition is a polymer that, when dissolved at 20° C. in an aqueous solution at 2% (w/v), preferably has an apparent viscosity of 1 to 50 000 mPa·s, more preferably of 1 to 10 000 mPa·s, and most preferably of 5 to 100 mPa·s. For example, preferred pharmaceutically acceptable polymers can be selected from the group comprising:

homopolymers of N-vinyl lactams, especially polyvinylpyrrolidone (PVP), copolymers of a N-vinyl lactam and and one or more comonomers copolymerizable therewith, the comonomers being selected from nitrogen-containing monomers and oxygen-containing monomers; especially a copolymer of N-vinyl pyrrolidone and a vinyl carboxylate, preferred examples being a copolymer of N-vinyl pyrrolidone and vinyl acetate or a copolymer of N-vinyl pyrrolidone and vinyl propionate;

cellulose esters and cellulose ethers, in particular methylcellulose and ethylcellulose, hydroxyalkylcelluloses, in particular hydroxypropylcellulose, hydroxyalkyl-alkylcelluloses, in particular hydroxypropylmethylcellulose, cellulose phthalates or succinates, in particular cellulose acetate phthalate and hydroxypropylmethylcellulose phthalate, hydroxypropylmethylcellulose succinate or hydroxypropylmethylcellulose acetate succinate;

polyvinyl alcohol-polyethylene glycol-graft copolymers (available as Kollicoat® IR from BASF AG, Ludwigshafen, Germany);

high molecular polyalkylene oxides such as polyethylene oxide and polypropylene oxide and copolymers of ethylene oxide and propylene oxide;

polyacrylates and polymethacrylates such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates) and poly(hydroxyalkyl methacrylates), poly(ethylacrylate-methylmethacrylate-trimethyl-ammonioethyl methacrylate chloride);

polyacrylamides;

vinyl acetate polymers such as copolymers of vinyl acetate and crotonic acid, partially hydrolyzed polyvinyl acetate (also referred to as partially saponified "polyvinyl alcohol");

polyvinyl alcohol;

poly(hydroxy acids) such as poly(lactic acid), poly(glycolic acid), polylactide-co-glycolide, poly(3-hydroxybutyrate) and poly(3-hydroxybutyrate-co-3-hydroxyvalerate); or mixtures of one or more thereof.

Among these, homopolymers or copolymers of N-vinyl pyrrolidone, in particular a copolymer of N-vinyl pyrrolidone and vinyl acetate, are preferred. A particularly preferred polymer is a copolymer of 60% by weight of the copolymer N-vinyl pyrrolidone and 40% by weight of the copolymer vinyl acetate.

Hydroxypropylcellulose is another example of a particularly preferred polymer.

Active ingredients used in the process according to the present invention are biologically active agents and include those which exert a local physiological effect, as well as those which exert a systemic effect, after oral administration. The invention is particularly useful for water-insoluble or poorly water-soluble (or "lipophilic") compounds. Compounds are considered water-insoluble or poorly water-soluble when their solubility in water at 25° C. is less than 1 g/100 ml.

Examples of suitable active substances include, but are not limited to:

analgesic and anti-inflammatory drugs such as fentanyl, indomethacin, ibuprofen, naproxene, diclofenac, diclofenac sodium, fenoprofen, acetylsalicylic acid, ketoprofen, nabumetone, paracetamol, piroxicam, meloxicam, tramadol, and COX-2 inhibitors such as celecoxib and rofecoxib;

anti-arrhythmic drugs such as procainamide, quinidine and verapamil;

antibacterial and antiprotozoal agents such as amoxicillin, ampicillin, benzathine penicillin, benzylpenicillin, cefaclor, cefadroxil, cefprozil, cefuroxime axetil, cephalexin, chloramphenicol, chloroquine, ciprofloxacin, clarithromycin, clavulanic acid, clindamycin, doxyxycline, erythromycin, flucloxacillin sodium, halofantrine, isoniazid, kanamycin sulphate, lincomycin, mefloquine, minocycline, nafcillin sodium, nalidixic acid, neomycin, nortloxacin, ofloxacin, oxacillin, phenoxymethyl-penicillin potassium, pyrimethamine-sulfadoxine and streptomycin;

anti-coagulants such as warfarin;

antidepressants such as amitriptyline, amoxapine, butriptyline, clomipramine, desipramine, dothiepin, doxepin, fluoxetine, reboxetine, aminepetine, selegiline, gepirone, imipramine, lithium carbonate, mianserin, milnacipran, nortriptyline, paroxetine, sertraline and 3-[2-[3,4-dihydrobenzofuro[3,2-c]pyridin-2(1H)-yl]ethyl]-2-methyl-4H-pyrido[1,2-a]pyrimidin-4-one;

anti-diabetic drugs such as glibenclamide and metformin;

anti-epileptic drugs such as carbamazepine, clonazepam, ethosuximide, gabapentin, lamotrigine, levetiracetam, phenobarbitone, phenytoin, primidone, tiagabine, topiramate, valpromide and vigabatrin;

antifungal agents such as amphotericin, clotrimazole, econazole, fluconazole, flucytosine, griseofulvin, itraconazole, ketoconazole, miconazole nitrate, nystatin, terbinafine and voriconazole;

antihistamines such as astemizole, cinnarizine, cyproheptadine, decarboethoxyloratadine, fexofenadine, flunarizine, levocabastine, loratadine, norastemizole, oxatomide, promethazine and terfenadine;

anti-hypertensive drugs such as captopril, enalapril, ketanserin, lisinopril, minoxidil, prazosin, ramipril, reserpine, terazosin and telmisartan;

anti-muscarinic agents such as atropine sulphate and hyoscine;

antineoplastic agents and antimetabolites such as platinum compounds, such as cisplatin and carboplatin; taxanes such as paclitaxel and docetaxel; tecans such as camptothecin, irinotecan and topotecan; vinca alkaloids such as vinblastine, vindecine, vincristine and vinorelbine; nucleoside derivatives and folic acid antagonists such as 5-fluorouracil, capecitabine, gemcitabine, mercaptopurine, thioguanine, cladribine and methotrexate; alkylating agents such as the nitrogen mustards, e.g. cyclophosphamide, chlorambucil, chiormethine, iphosphamide, melphalan, or the nitrosoureas, e.g. carmustine, lomustine, or other alkylating agents, e.g. busulphan, dacarbazine, procarbazine, thiotepa; antibiotics such as daunorubicin, doxorubicin, idarubicin, epirubicin, bleomycin, dactinomycin and mitomycin; HER 2 antibodies such as trastuzumab; podophyllotoxin derivatives such as etoposide and teniposide; famesyl transferase inhibitors; anthrachinon derivatives such as mitoxantron;

anti-migraine drugs such as alniditan, naratriptan and sumatriptan;

anti-Parkinsonian drugs such as bromocryptine mesylate, levodopa and selegiline;

antipsychotic, hypnotic and sedating agents such as alprazolam, buspirone, chlordiazepoxide, chlorpromazine, clozapine, diazepam, flupenthixol, fluphenazine, flurazepam, 9-hydroxyrisperidone, lorazepam, mazapertine, olanzapine, oxazepam, pimozide, pipamperone, piracetam, promazine, risperidone, selfotel, seroquel, sertindole, sulpiride, temazepam, thiothixene, triazolam, trifluperidol, ziprasidone and zolpidem;

anti-stroke agents such as lubeluzole, lubeluzole oxide, riluzole, aptiganel, eliprodil and remacemide;

antitussives such as dextromethorphan and laevodropropizine;

antivirals such as acyclovir, ganciclovir, loviride, tivirapine, zidovudine, lamivudine, zidovudine/lamivudine, didanosine, zalcitabine, stavudine, abacavir, lopinavir, amprenavir, nevirapine, efavirenz, delavirdine, indinavir, nelfinavir, ritonavir, saquinavir, adefovir and hydroxyurea;

beta-adrenoceptor blocking agents such as atenolol, carvedilol, metoprolol, nebivolol and propanolol;

cardiac inotropic agents such as amrinone, digitoxin, digoxin and milrinone;

corticosteroids such as beclomethasone dipropionate, betamethasone, budesonide, dexamethasone, hydrocortisone, methylprednisolone, prednisolone, prednisone and triamcinolone;
disinfectants such as chlorhexidine;
diuretics such as acetazolamide, furosemide, hydrochlorothiazide and isosorbide;
enzymes;
essential oils such as anethole, anise oil, caraway, cardamom, cassia oil, cineole, cinnamon oil, clove oil, coriander oil, dementholised mint oil, dill oil, eucalyptus oil, eugenol, ginger, lemon oil, mustard oil, neroli oil, nutmeg oil, orange oil, peppermint, sage, spearmint, terpineol and thyme;
gastro-intestinal agents such as cimetidine, cisapride, clebopride, diphenoxylate, domperidone, famotidine, lansoprazole, loperamide, loperamide oxide, mesalazine, metoclopramide, mosapride, nizatidine, norcisapride, olsalazine, omeprazole, pantoprazole, perprazole, prucalopride, rabeprazole, ranitidine, ridogrel and sulphasalazine;
haemostatics such as aminocaproic acid;
lipid regulating agents such as atorvastatin, fenofibrate, fenofibric acid, lovastatin, pravastatin, probucol and simvastatin;
local anaesthetics such as benzocaine and lignocaine;
opioid analgesics such as buprenorphine, codeine, dextromoramide, dihydrocodeine, hydrocodone, oxycodone and morphine;
parasympathomimetics and anti-dementia drugs such as AIT-082, eptastigmine, galanthamine, metrifonate, milameline, neostigmine, physostigmine, tacrine, donepezil, rivastigmine, sabcomeline, talsaclidine, xanomeline, memantine and lazabemide;
peptides and proteins such as antibodies, becaplermin, cyclosporine, tacrolimus, erythropoietin, immunoglobulins and insuline;
sex hormones such as oestrogens: conjugated oestrogens, ethinyloestradiol, mestranol, oestradiol, oestriol, oestrone; progestogens; chlormadinone acetate, cyproterone acetate, 17-deacetyl norgestimate, desogestrel, dienogest, dydrogesterone, ethynodiol diacetate, gestodene, 3-keto desogestrel, levonorgestrel, lynestrenol, medroxy-progesterone acetate, megestrol, norethindrone, norethindrone acetate, norethisterone, norethisterone acetate, norethynodrel, norgestimate, norgestrel, norgestrienone, progesterone and quingestanol acetate;
stimulating agents such as sildenafil, vardenafil;
vasodilators such as amlodipine, buflomedil, amyl nitrite, diltiazem, dipyridamole, glyceryl trinitrate, isosorbide dinitrate, lidoflazine, molsidomine, nicardipine, nifedipine, oxpentifylline and pentaerythritol tetranitrate;
their N-oxides, their pharmaceutically acceptable acid or base addition salts and their stereochemically isomeric forms.

Pharmaceutically acceptable acid addition salts comprise the acid addition salt forms which can be obtained conveniently by treating the base form of the active ingredient with appropriate organic and anorganic acids.

Active ingredients containing an acidic proton may be converted into their non-toxic metal or amine addition salt forms by treatment with appropriate organic and inorganic bases.

The term addition salt also comprises the hydrates and solvent addition forms which the active ingredients are able to form. Examples of such forms are hydrates, alcoholates and the like.

The N-oxide forms of the active ingredients comprise those active ingredients in which one or several nitrogen atoms are oxidized to the so-called N-oxide.

The term "stereochemically isomeric forms" defines all possible stereoisomeric forms which the active ingredients may possess. In particular, stereogenic centers may have the R- or S-configuration and active ingredients containing one or more double bonds may have the E- or Z-configuration.

The term "pharmaceutically acceptable surfactant" as used herein refers to a pharmaceutically acceptable ionic or nonionic surfactant. Incorporation of surfactants is especially preferred for matrices containing poorly water-soluble active ingredients. The surfactant may effectuate an instantaneous emulsification of the active ingredient released from the dosage form and/or prevent precipitation of the active ingredient in the aqueous fluids of the gastrointestinal tract.

Preferred surfactants are selected from:
polyoxyethylene alkyl ethers, e.g. polyoxyethylene (3) lauryl ether, polyoxyethylene (5) cetyl ether, polyoxyethylene (2) stearyl ether, polyoxyethylene (5) stearyl ether; polyoxyethylene alkylaryl ethers, e.g. polyoxyethylene (2) nonylphenyl ether, polyoxyethylene (3) nonylphenyl ether, polyoxyethylene (4) nonylphenyl ether or polyoxyethylene (3) octylphenyl ether;
polyethylene glycol fatty acid esters, e.g. PEG-200 monolaurate, PEG-200 dilaurate, PEG-300 dilaurate, PEG-400 dilaurate, PEG-300 distearate or PEG-300 dioleate;
alkylene glycol fatty acid mono esters, e.g. propylene glycol monolaurate (Lauroglycol®);
sucrose fatty acid esters, e.g. sucrose monostearate, sucrose distearate, sucrose monolaurate or sucrose dilaurate;
sorbitan fatty acid mono esters such as sorbitan mono laurate (Span® 20), sorbitan monooleate, sorbitan monopalmitate (Span® 40), or sorbitan stearate,
polyoxyethylene castor oil derivates, e.g. polyoxyethyleneglycerol triricinoleate or polyoxyl 35 castor oil (Cremophor® EL; BASF Corp.) or polyoxyethyleneglycerol oxystearate such as polyethylenglycol 40 hydrogenated castor oil (Cremophor® RH 40; BASF Corp.) or polyethylenglycol 60 hydrogenated castor oil (Cremophor® RH 60; BASF Corp.); or
block copolymers of ethylene oxide and propylene oxide, also known as polyoxyethylene polyoxypropylene block copolymers or polyoxyethylene polypropyleneglycol such as Poloxamer® 124, Poloxamer® 188, Poloxamer® 237, Poloxamer® 388, or Poloxamer® 407 (BASF Corp.); or
mono fatty acid esters of polyoxyethylene (20) sorbitan, e.g. polyoxyethylene (20) sorbitan monooleate (Tween® 80), polyoxyethylene (20) sorbitan monostearate (Tween® 60), polyoxyethylene (20) sorbitan monopalmitate (Tween® 40), polyoxyethylene (20) sorbitan monolaurate (Tween® 20), or mixtures of one or more thereof.

Various additives may be included in the melt, for example flow regulators such as colloidal silica; lubricants, fillers, disintegrants, or plasticizers, stabilizers or preservatives.

Various other additives may be used, for example dyes such as azo dyes, organic or inorganic pigments such as iron oxides or titanium dioxide, or dyes of natural origin; stabilizers such as antioxidants, light stabilizers, radical scavengers and stabilizers against microbial attack.

These additives may be incorporated into the mixture of active ingredient and polymer at any appropriate stage of the process. For ease of handling it is, however, convenient to include such additives in a powdery mixture of the matrix-forming agent and the active ingredient that is being fed into the extruder.

The extrudate exiting from the extruder ranges from pasty to viscous. Before allowing the extrudate to solidify, the extrudate may be directly shaped into virtually any desired shape. Shaping of the extrudate may be conveniently carried out by a calender with two counter-rotating rollers with mutually matching depressions on their surface. A broad range of tablet forms can be attained by using rollers with different forms of depressions. If the rollers do not have depressions on their surface, films can be obtained. Alternatively, the extrudate is moulded into the desired shape by injection-moulding. Alternatively, the extrudate is subjected to profile extrusion and cut into pieces, either before (hot-cut) or after solidification (cold-cut).

Additionally, foams can be formed if the extrudate contains a propellant such as a gas, e.g. carbon dioxide, or a volatile compound, e.g. a low molecular weight hydrocarbon, or a compound that is thermally decomposable to a gas. The propellant is dissolved in the extrudate under the relatively high pressure conditions within the extruder and, when the extrudate emerges from the extruder die, the pressure is suddenly released. Thus the solvability of the propellant is decreased and/or the propellant vaporises so that a foam is formed.

Optionally, the resulting solid dispersion product is milled or ground to granules. The granules may then be compacted. Compacting means a process whereby a powder mass comprising the granules is condensed under high pressure in order to obtain a compact with low porosity, e.g. a tablet. Compression of the powder mass is usually done in a tablet press, more specifically in a steel die between two moving punches.

Preferably, at least one additive selected from flow regulators, disintegrants, bulking agents (fillers) and lubricants is used in compacting the granules. Disintegrants promote a rapid disintegration of the compact in the stomach and keep the granules which are liberated separate from one another. Suitable disintegrants are crosslinked polymers such as crosslinked polyvinyl pyrrolidone and crosslinked sodium carboxymethylcellulose. Suitable bulking agents (also referred to as "fillers") are selected from lactose, calcium hydrogenphosphate, microcrystalline cellulose (Avicel®), silicates, in particular silicium dioxide, talc, potato or corn starch, and isomalt.

Suitable flow regulators are selected from highly dispersed silica (Aerosil®), and animal or vegetable fats or waxes.

A lubricant is preferably used in compacting the granules. Suitable lubricants are selected from polyethylene glycol (e.g., having a Mw of from 1000 to 6000), magnesium and calcium stearates, sodium stearyl fumarate, and the like.

EXEMPLIFICATION

The following examples will serve to further illustrate the invention without limiting it.

Figure 4:
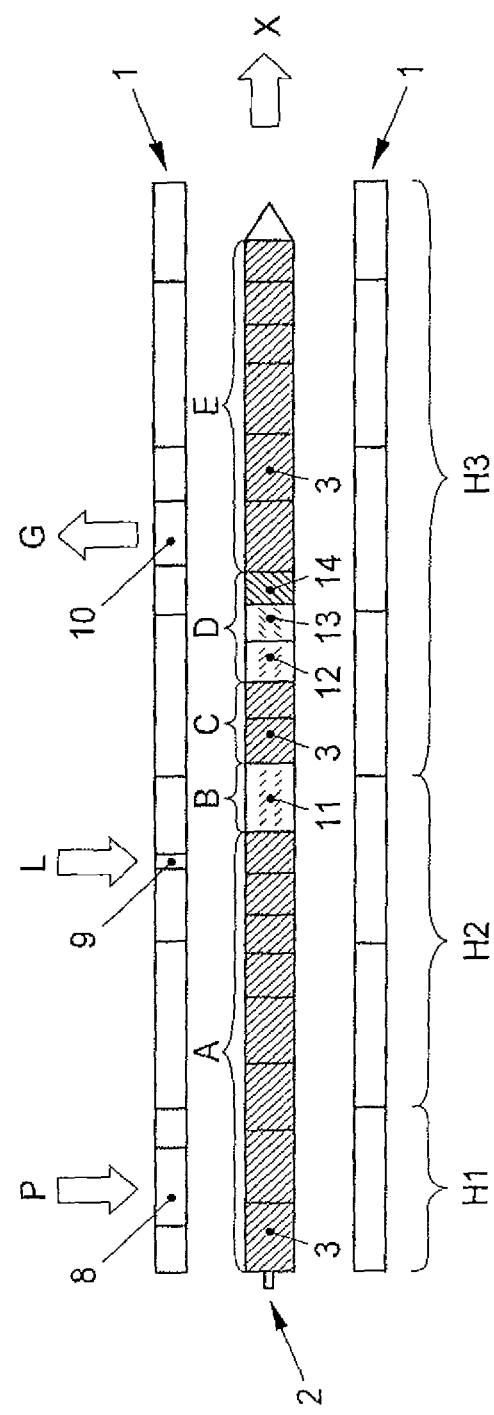
FIG. 4 shows schematically a sectional view of the extruder that was used for an example in accordance with the process according to the present invention.

As the extruders shown in FIGS. 1 and 4 are generally similar, the general arrangement of the extruder is described with reference to FIG. 1.

The extruder is known per se. It has been used for producing a solid dispersion of an active ingredient in a matrix-forming agent. The extruder comprises a housing or barrel 1 divided into several sections in a longitudinal direction. On the upstream side of the extruder, an opening 8 is provided for feeding a powder P of the active ingredient and the matrix-forming agent. Usually, a hopper is placed on this opening so that the powder P can be easily fed into the barrel 1 of the extruder. In conveying direction X of the extruder, i.e. downstream from the opening 8, a further opening 9 for dosing a further component L, such as a surfactant, is provided. Here, the surfactant is pumped in liquid or liquefied form or dosed in solid form to the inside of barrel 1. Even further downstream, another opening 10 is provided for sucking gas G from the inside of the barrel 1 to the outside of the barrel 1. The barrel 1 ends in conveying direction X in a die, where the dispersion is expelled.

Furthermore, the barrel 1 of the extruder is divided into three heating zones H1, H2 and H3. The temperature of the barrel 1 in these heating zones H1, H2 and H3 can be controlled in order to control the melting of the dispersion of the active ingredient and the matrix-forming agent.

Within the barrel 1 of the extruder, two parallel shafts 2 are arranged, one of which is shown in the sectional views of FIGS. 1 to 4. Preferably, the shafts 2 are co-rotating. The shafts 2 are equipped with processing elements disposed axially one behind the other. The processing elements are arranged within the extruder barrel 1 so that the radially outermost portions of the processing elements are adjacent to the inner wall of the barrel 1. Only a very small gap is formed between the outermost portions of the processing element and the inner wall of the barrel 1. As FIGS. 1 to 4 are only schematic representations to show the different zones of the extruder in a longitudinal direction, the shafts 2 with the processing elements and the extruder barrel 1 are shown apart from one another.

The shaft 2 with the processing elements is divided in several sections. In the following, these sections are described with respect to FIGS. 1 to 4.

FIG. 1 shows an arrangement of processing elements for a first embodiment of the process according to the present invention. The section furthermost upstream is a feeding and conveying section A. The upstream side of this section A is adjacent to opening 8 for feeding powder P into the barrel 1. On the downstream side of section A, the opening 9 of the barrel 1 is provided for feeding a surfactant to the inside of the barrel 1. The processing elements of the feeding and conveying section A are formed by screw-type elements 3, which form an endless screw having the feed direction X and a uniform pitch flight. Therefore, in section A, the powder P is fed into the extruder 1 and conveyed in the downstream direction X. The heating zones H1 and H2 of the extruder 1 are controlled so that the substances within the barrel 1 start to melt at the end of the feeding and conveying section A.

Downstream from section A, a reverse-flight section R is arranged. Reverse-flight section R comprises reverse-flight elements 14-1, 14-2 and 14-3. Between reverse-flight element 14-1 and reverse-flight element 14-2, a screw-type element 3 is arranged having the same configuration as the screw-type elements 3 of the feeding and conveying section A. Between reverse-flight elements 14-2 and 14-3, two screw-type elements 3 are arranged which are also identical to the screw-type elements 3 of the feeding and conveying section A. The length of the screw-type elements 3 between the reverse-flight element 14-2 and 14-3 is twice that of the screw-type element 3 between reverse-flight elements 14-1 and 14-2. The geometry of the reverse-flight elements 14-1 to 14-3 is the same as the geometry of screw-type elements 3 with the difference that the screw-pitch has the opposite algebraic sign. However, the screw pitch of the reverse-flight elements 14-1 to 14-3 may also be in a range from −0.5 times to −1.5 times, preferably from −0.8 times to −1.2 times, the screw-pitch of the screw-type elements 3 of the feeding and conveying section and/or the screw-type element(s) arranged between the two reverse-flight elements 14-1 to 14-3

Downstream of the reverse-flight section R, a discharge section E is arranged. The shaft 2 of the extruder in discharge section E is equipped with screw-type elements 3, which are identical to the elements used in section A. In discharge section E the melt is only fed to the die of the extruder.

In practice a polymer and the matrix-forming agent are fed to the inside of barrel 1 of the extruder through opening 8. The matrix-forming agent and the active ingredient are conveyed by screw elements 3 to reverse-flight element 14-1. Heating zones H1 and H2 are heated to a temperature so that the polymer and the matrix-forming agent start to melt just before mixing element 11. Here as well, surfactants are fed through opening 9 to the inside of the barrel 1. The melt then passes reverse-flight element 14-1 and is conveyed by the screw-type element between reverse-flight elements 14-1 and 14-2 to the second reverse-flight element 14-2. The melt then passes reverse-flight element 14-2 and is conveyed by the screw-type elements between reverse-flight elements 14-2 and 14-3 to the third reverse-flight element 14-3. In the reverse-flight section R, the main mixing and melting effect is performed. Thereafter, the uniform extrudate is conveyed by screw elements 3 of discharging section E to the die of the extruder.

FIG. 2 shows another arrangement of processing elements for a second embodiment of the process according to the present invention.

The processing elements of sections A and E are the same as in the arrangement of processing elements shown in FIG. 1. However, section A may be shorter than section A as shown in FIG. 1, as the reverse-flight section R of the arrangement shown in FIG. 2 is longer than the reverse-flight section R of the arrangement shown in FIG. 1.

Downstream from section A, a reverse-flight section R is arranged. The reverse-flight section R of this embodiment comprises a reverse-flight element 14-1, followed by screw-type elements 3, which are identical to the screw-type element 3 arranged between reverse-flight elements 14-1 and 14-2 shown in FIG. 1. There follows a reverse-flight element 14-2, which is identical to reverse-flight element 14-1. Subsequently, screw-type elements 3 are arranged, which are identical to screw-type elements 3 with respect to shape as well as to length, which are arranged between reverse-flight elements 14-1 and 14-2. Then, another reverse-flight element 14-3 is arranged, which is identical to the first two reverse-flight elements 14-1 and 14-2. Subsequently, further screw-type elements 3 are arranged, which are identical in shape and length to the screw-type elements 3 arranged between reverse-flight elements 14-1 and 14-2 and between 14-2 and 14-3. Finally, a reverse-flight element 14-4 is arranged at the end of reverse-flight section R, which is identical to the preceding reverse-flight elements 14-1 to 14-3.

The reverse-flight elements used in the arrangements shown in FIGS. 1 and 2 are elements whose basic shape is that of a screw element. Such an element differs from conventionally known kneading elements or modified kneading elements. In particular, a kneading element allows an enhanced flow of the extrudate between its periphery ridges (i.e., its outer edge) and the barrel or bore of the extruder. The reverse-flight elements which are based on a screw-type element according to the invention do only allow a small amount of the extrudate to flow between the edge of the screw and the barrel or bore of the extruder.

Furthermore, the reverse-flight elements have not a plane surface area with a normal parallel and opposite to the general conveying direction. Moreover, the reverse-flight element does not have abutting faces that are perpendicular to the general conveying direction.

Figure 3:
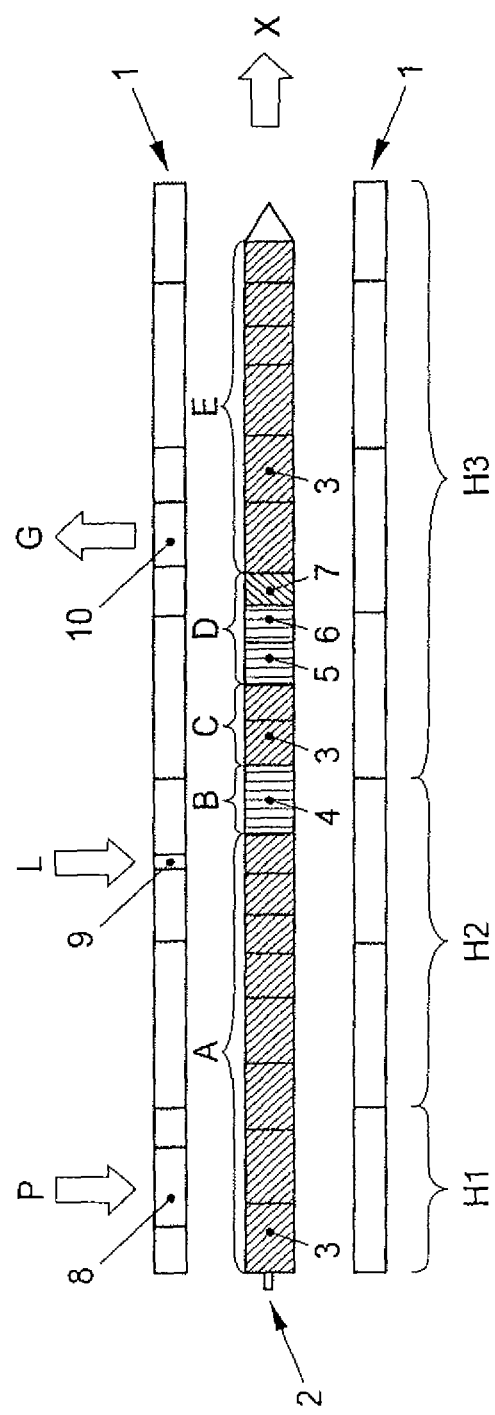
FIG. 3 shows schematically a sectional view of the extruder comprising screws comprising paddle means or kneading blocks that was used for an example in accordance with the process according to the present invention.

With respect to FIG. 3, a further arrangement of processing elements for a third embodiment of the process according to the present invention is described.

The processing elements of sections A and E are the same as in the arrangement of processing elements shown in FIG. 1. However, section A may be shorter than section A as shown in FIG. 1.

Downstream from section A, a mixing section B is arranged. The processing elements in mixing section B comprises so-called paddle means or kneading blocks 4, which consist of disk cams.

On the downstream side of mixing section B, an intermediate conveying section C is formed. The processing elements of intermediate section C are the same screw-type elements 3 used in the feeding and conveying section A. Therefore, intermediate conveying section C only conveys the melt from mixing section B to the next section.

Downstream of the intermediate conveying section C, a reverse-flight or second mixing section D is arranged. In section D the processing elements are paddle means or kneading blocks 5 and 6. On the downstream side of kneading block 6, a reverse-flight element 7 is positioned. The reverse-flight element 7 serves to create sufficient back-pressure to allow for a desired degree of mixing and/or homogenization. It accumulates the material into mixing sections B and D. The reverse-flight element 7 is derived from a screw-type element having a reverse-pitch flight, such that it conveys the melt in an opposite direction relative to the general conveying direction X of the extruder. The reverse-flight element 7 is identical to reverse-flight elements 14 shown in FIGS. 1 and 2.

It should be mentioned that the use of paddle means or kneading blocks 5 and 6 is known per se. However, the use of a reverse-flight element 7 in connection with the arrangement of the extruder shown in FIG. 3 is not known per se.

Downstream from the second mixing section D, a discharging section E is arranged. The shaft 2 of the extruder 2 is equipped with screw-type elements 3, which are identical to the elements used in sections A and C. In discharging section E, the melt is only fed to the die of the extruder.

With respect to FIG. 4, a further arrangement of processing elements for a forth embodiment of the process according to the present invention is described.

The processing elements of sections A, C and E are the same as in the arrangement of processing elements shown in FIG. 3. The arrangement of FIG. 4 differs from the arrangement of FIG. 3 in the processing elements of sections B and D. In section B the shaft 2 of the extruder used in the forth embodiment is equipped with a particular mixing element 11 instead of the paddle means or kneading blocks 4 of section B of the third embodiment. The mixing element is described in greater detail below with reference to FIGS. 5 to 7. Furthermore, in the second mixing section D of the extruder of the forth embodiment, the shaft is equipped with particular mixing elements 12, 13 instead of the paddle means or kneading blocks 5 and 6 of section D of the third embodiment. Mixing elements 12,13 are again described in greater detail below with reference to FIGS. 5 to 7. Mixing elements 12,13 may be identical to mixing element 11 of the first mixing section B. However, in the embodiment shown in FIG. 5, the mixing element is divided into portions 12 and 13, portion 12 having a positive feeding direction and portion 13 having a negative feeding direction or a reverse flight.

Downstream from mixing elements 12,13, a reverse-flight element 14 is arranged, which corresponds to the reverse-flight element 14-1 to 14-3 and 7 described above.

It should be noted that the length of kneading blocks 4 corresponds to the length of the mixing element 11 and the length of kneading blocks 5, 6 corresponds to the length of mixing elements 12,13.

Downstream from the second mixing section D, a discharging section E is arranged. The shaft 2 of the extruder is equipped with screw-type elements 3, which are identical to the elements used in sections A and C. In discharging section E, the melt is only fed to the die of the extruder.

In practice a polymer and the matrix-forming agent are fed to the inside of barrel 1 of the extruder through opening 8. The matrix-forming agent and the active ingredient are conveyed by screw elements 3 to mixing element 11. Heating zones H1 and H2 are heated to a temperature so that the polymer and the matrix-forming agent start to melt just before mixing element 11. Here as well, surfactants are fed through opening 9 to the inside of the barrel 1. The melt then passes mixing element 11 and is conveyed by screw elements 3 of the intermediate conveying section C to the second mixing section D comprising mixing elements 12,13 and thereafter reverse-flight element 14. Here, the main mixing and melting effect is performed. Thereafter, the uniform extrudate is conveyed by screw elements 3 of discharging section E to the die of the extruder.

In the following, examples of mixing elements that may be used in mixing sections B and D are described with reference to FIGS. 5 to 7.

In general, the mixing elements 15, 20, and 24 shown in FIGS. 5 to 7 and which may be used as mixing elements 11 to 13 on the two shafts 2 have a transverse profile 23 composed of three circular arcs. One circular arc has a diameter corresponding to the diameter of the outer screw, another circular arc has a diameter corresponding to the diameter of the screw core, and a further circular arc has a diameter whose radius corresponds to the center distance of the two elements of the mixing element (cf. EP-B-0002 131).

Further, the mixing elements 15, 20, and 24 comprise a bore 22 having projections for engagement with grooves of the shaft 2 so that the mixing elements 15, 20, and 24 can be rotated together with the shaft 2.

Figure 5B:
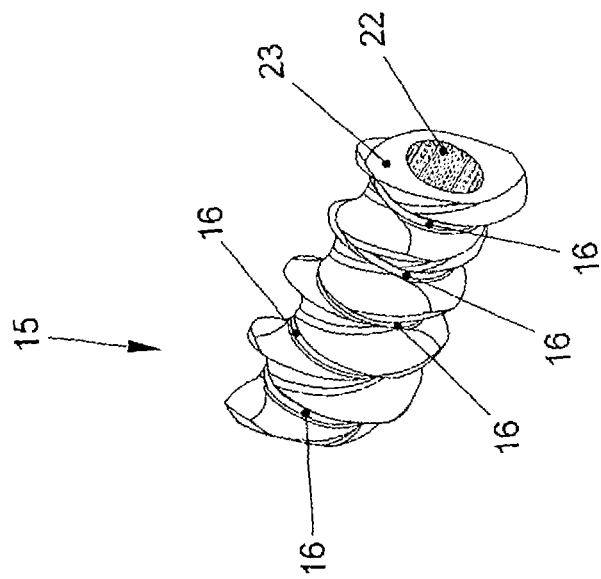
FIG. 5A and FIG. 5B show one preferred embodiment of a mixing element in accordance with the present invention.
Figure 5A:
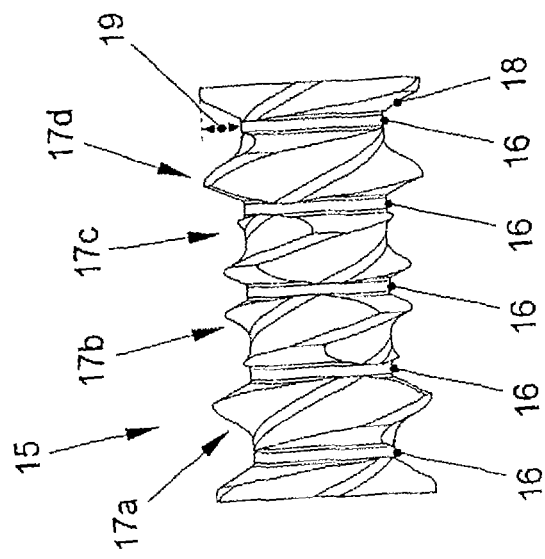

As can be seen from FIGS. 5A and 5B, the mixing element 15 has five ring portions 16 that are concentric with the shaft axis and disposed a distance apart from another. The ring portions 16 are obtained by grooves turned into the mixing element 15. The angle of the flanks 18 of the grooves to the shaft axis is about 60 degrees. The height of the annular gaps 19 between the ring portions 16 and the inner wall of the extruder barrel 1 is about the flight depth, i.e. the difference between the core diameter and the outside screw diameter. The diameter of the ring portions 8 thus corresponds to the core diameter of the screw.

In mixing element 15 a continuous screw flight may be formed which is interrupted only by the turned grooves with ring portions 16. In contrast, screw portions of the mixing element 15 between ring portions 16 may also be disposed at a progressive angular offset from each other with the same direction of rotation.

The screw sections 17a, 17b, 17c, 17d between the ring portion 16 of mixing element 15 in the embodiment shown in FIGS. 5A and 5B have the same screw pitch. The mixing element 15 shown in FIGS. 5A and 5B may be used in particular as mixing element 11 in mixing section B as shown in FIG. 5.

A further example of a mixing element 20 is shown in FIGS. 6A and 6B. Mixing element 20 differs from mixing element 15 in screw sections 21a, 21b, 21c, 21d between ring portions 16. Screw sections 21a and 21b may correspond to 17a and 17b of mixing element 15. However, screw sections 21c and 21d of mixing element 20 differ from screw sections 17c and 17d of mixing element 15. Namely, screw sections 21c and 21d have a reverse-flight screw so that these sections 21c and 21d convey the melt in an opposite direction relative to the general conveying direction X of the extruder and the conveying direction of screw sections 21a and 21b.

Screw sections 21a and 21b may be formed integrally with screw sections 21c and 21d as shown in FIGS. 6A and 6B. However, two mixing elements may also be provided, one comprising screw sections 21a and 21b and the other comprising screw sections 21c and 21d. Mixing element 20 may correspond to mixing elements 12, 13 of the second mixing section D shown in FIG. 5.

A further example of a mixing element 24 is shown in FIGS. 7A and 7B. As for the screw sections 26a, 26b, 26c and 26d, the mixing element 24 is similar to mixing element 20 shown in FIGS. 6A and 6B. Screw section 26a and 26b have a positive screw flight and screw section 26c and 26d have a negative screw flight or reverse-flight screw.

Furthermore, mixing element 24 differs from mixing elements 20 and 15 in the annular gap 27 between the ring portions 25 and the extruder barrel 1. In the example of mixing element 24, the height of the annular gaps 27 is about half of the flight depth, i.e. half the difference between the core diameter and the outside screw diameter. The diameter of the ring portions 8 thus corresponds approximately to the center distance of the two shafts from each other. The larger diameter of ring portions 25 relative to the diameter of ring portions 16 of mixing elements 20 and 15 provides a barrier for the melt. It has been found that such a barrier is advantageous if the mixing element 24 is used as mixing elements 12, 13 in the second mixing section D as shown in FIG. 5. The barrier provides a compacting zone within the extruder in which the pressure of the extrudate is raised on the substance supply side.

The following provides examples in which the same solid dispersion of an active ingredient in a polymer has been produced by, first, the extruder with the screw arrangement shown in FIG. 3 as a comparative example and, second, the extruder with the screw arrangement shown in FIG. 5.

Example 1

An extrudate was prepared from the ingredients given in Table 1.

TABLE 1

Compositions of Extrudates

|  | Formulation |
| --- | --- |
| Ibuprofen 25 USP (active ingredient) | 40 wt % |
| Kollidon Typ CL (polymer) | 5 wt % |
| Povidon Typ K30 (polymer) | 23.8 wt % |
| Sodium carbonate | 20 wt % |
| Isomalt Typ PF | 10.2 wt % |
| Aerosil Typ 200 (glidant) | 1.0 wt % |

The active ingredients, the polymer and the glidant were thoroughly mixed and the resulting powder was fed into a twin-screw extruder (ZSK-40, manufactured by Werner & Pfleiderer, Germany). The screw configuration comprised reverse-flight elements in addition to conveying elements and is shown in FIG. 1. During the extrusion process, powder mixture was melted. Vacuum was applied to the mixture in the last third of the extruder The process parameters are detailed in Table 2. Subsequent to the extrusion step, the material was formed on a calendar and cooled to reveal a band of lentil-shaped extrudate.

TABLE 2

Process Parameters

|  | Formulation |
|---|---|
| Formulation Flow rate extruder [kg/h] | 17.0 |
| Screw speed [rpm] | 100 |
| Vacuum [mbar] | 150 |
| Temperature |  |
| barrel 1 [° C.] | 25 |
| barrel 2 + 3 [° C.] | 80 |
| barrel 4 – 6 [° C.] | 130 |

The properties of the extrudate were acceptable which means that the extrudate could be shaped by calendaring.

Example 2

An extrudate was prepared from the ingredients given in Table 3.

TABLE 3

Composition of extrudates

|  | Formulation 1 | Formulation 2 |
|---|---|---|
| Lopinavir (active ingredient) | 24.00% | 23.49% |
| Ritonavir (active ingredient) | 6.00% | 5.87% |
| Copovidone (polymer) | 63.00% | 61.66% |
| Emulsifier mixture | 6.0% | 8.0% |
| Aerosil 200 (glidant) | 1.00% | 0.98% |

The active ingredients, the polymer and the glidant were thoroughly mixed and the resulting powder was fed into a twin-screw extruder (ZSK-40, manufactured by Werner & Pfleiderer, Germany). The screw configuration comprised kneading blocks in addition to conveying elements and is shown in FIG. 3. The emulsifiers were fed into the extruder by means of a liquid dosing pump. The emulsifiers were added at a position immediately before the material in the extruder reaches the first kneading block section. During the extrusion process, the liquid emulsifiers were blended with the powder and the mixture was melted. Vacuum was applied to the mixture in the last third of the extruder. The process parameters are detailed in Table 4. Subsequent to the extrusion step, the material was formed on a calendar and cooled to reveal a band of lentil-shaped extrudate.

TABLE 4

Process Parameters

|  | Formulation 1 | Formulation 2 |
|---|---|---|
| Feeding Rate |  |  |
| Powder [g/h] | 15.7 | 15.7 |
| liquid [g/h] | 1.0 | 1.36 |
| Screw speed [rpm] | 100 | 120 |
| Vacuum [mbar] | 350 | 200 |
| Temperature |  |  |
| barrel 1 [° C.] | 20 | 20 |
| barrel 2 + 3 [° C.] | 80 | 80 |
| barrel 4 – 6 [° C.] | 100 | 100 |
| die head [° C.] | 125 | 125 |
| die [° C.] | 125 | 125 |
| Torque [% of engine power] | 35 | 35 |

TABLE 4-continued

Process Parameters

|  | Formulation 1 | Formulation 2 |
|---|---|---|
| Appearance of extrudate | Smooth, transparent | Smooth, transparent |
| Temperature of extrudate [° C.] | 125 | 127-128 |

Analytical test results for the extrudates are given in Table 5. The lopinavir/ritonavir content and the content of a major ritonavir degradation product were determined by HPLC. Water content was determined by Karl-Fischer-Titration, and tests for crystallinity were conducted by DSC.

TABLE 5

Analytical results of extrudates

|  | Formulation 1 | Formulation 2 |
|---|---|---|
| Crystallinity | None | None |
| Lopinavir | 102.3% | 101.5% |
| Ritonavir | 97.5% | 97.0% |
| Ritonavir degradation product | 0.28% | 0.37% |
| Relative amount ritonavir degradation product/ritonavir | 0.287% | 0.381% |
| Water content | 1.1% | 0.8% |

Example 3

Example 2 was repeated. However, the screws were designed differently: instead of kneading blocks, it comprised mixing elements. The configuration of this screw is depicted in FIG. 4. The kneading blocks in screw ZSK 40-54 (FIG. 3) are replaced by mixing elements with both mixing zones being equivalent in length. Mixing section B comprises a mixing element 15 according to FIG. 5; mixing section D comprises a mixing element 20 according to FIG. 6. The process parameters are given in Table 6, the analytical results are given in Table 7.

TABLE 6

Process Parameters

|  | Formulation 1 | Formulation 2 |
|---|---|---|
| Feeding Rate |  |  |
| Powder [g/h] | 15.7 | 15.7 |
| liquid [g/h] | 1.0 | 1.36 |
| Screw speed [rpm] | 100 | 120 |
| Vacuum [mbar] | 350 | 200 |
| Temperature |  |  |
| barrel 1 [° C.] | 20 | 20 |
| barrel 2 + 3 [° C.] | 80 | 80 |
| barrel 4 – 6 [° C.] | 100 | 100 |
| die head | 125 | 125 |
| die [° C.] | 125 | 125 |
| Torque [% of engine power] | 36 | 33 |
| Appearance of extrudate | Smooth, transparent | Smooth, transparent |
| Temperature of extrudate [° C.] | 123-124 | 124 |

TABLE 7

Analytical results of extrudates

| | Formulation 1 | Formulation 2 |
|---|---|---|
| Crystallinity | None | None |
| Lopinavir | 102.7% | 102.1% |
| Ritonavir | 99.4% | 99.7% |
| Ritonavir degradation product | 0.27% | 0.36% |
| Relative amount ritonavir degradation product/ritonavir | 0.272% | 0.361% |
| Water content | 1.3% | 0.9% |

From the results in Table 5 and Table 7 it is apparent that degradation is more pronounced during extrusion with a screw bearing kneading blocks than during a run with a screw containing mixing elements.

The higher degradation observed with Formulation 2 relative to Formulation 1 can be attributed to the process parameters. To homogeneously mix the higher emulsifier amount into the powder blend, both screw speed and extrusion temperature needed to be increased (Tables 4 and 6). The higher energy input not only led to the desired homogeneous extrudate, but also to an increase in degradation. Since an increase in screw speed usually goes along with some entrapment of air in the extrudate, the vacuum was increased for Formulation 2. An increased vacuum in turn increases the energy input, thereby contributing to the enhanced mixing. Another consequence is a lower water content of the product.

We claim:

1. A process for producing a solid dispersion of a pharmaceutical active ingredient which comprises feeding the pharmaceutical active ingredient and a matrix-forming agent to an extruder and forming a uniform extrudate, wherein at least 98% by weight of the total amount of active ingredient is present in an amorphous state:
   wherein the extruder comprises a housing, and at least two rotating shafts within said housing, wherein each of the shafts carries a plurality of processing elements disposed axially one behind the other, the processing elements defining
   (i) a feeding and conveying section,
   (ii) a first mixing section,
   (iii) an intermediate conveying section,
   (iv) a reverse-flight section, and
   (v) a discharging section,
   wherein the processing elements defining the first mixing section comprise at least one mixing element and
   the processing elements defining the reverse-flight section comprise at least one mixing element and downstream thereto at least one reverse-flight element,
   wherein the at least one reverse-flight element is based on a screw-type element having a conveying direction opposite to the general conveying direction of the extruder;
   wherein at least one mixing element is derived from a screw-type element, has recesses formed in the screw-flight of the screw-type element, and has a plurality of concentric ring portions formed by grooves turned into the screw-type element; and
   wherein the processing elements are sized and configured to provide a recurring sequence of pressure build-up that forces the pharmaceutical active ingredient through an annular gap between the extruder housing and ring portions of the mixing element with shearing action and elongation, followed by a reduction in pressure, thereby causing a defined and uniform but not undue stress on the pharmaceutical active ingredient, thereby avoiding high temperatures or high local shear forces that cause decomposition of the pharmaceutical active ingredient and preventing residues of extruded material from remaining within the extruder over extended periods of time; and
   wherein said mixing elements enable a sufficient degree of mixing or homogenization with less degradation of the active ingredient or formulation of other ingredients as compared to degradation of the active ingredient or formulation of other ingredients resulting from a process employing paddle means or mixing blocks.

2. The process of claim 1, wherein the processing elements defining the reverse-flight section comprise at least three reverse-flight elements wherein at least one positive-flight screw-type element is arranged between the respective successive reverse-flight elements.

3. The process of claim 2, wherein the length of the positive-flight screw-type element(s) arranged between the second and third reverse-flight element is in a range from 1 to 15 times the length of the positive-flight screw-type element(s) arranged between the first and second reverse-flight elements.

4. The process of claim 1, wherein the processing elements defining the reverse-flight section comprise at least four reverse-flight elements, wherein at least one positive-flight screw-type element is arranged between the respective successive reverse-flight elements, and wherein the positive-flight screw-type elements arranged between successive reverse-flight elements have the same length.

5. The process of claim 1, wherein at least one reverse-flight element is positioned downstream to the mixing element(s).

6. The process of claim 1, wherein at least one mixing element does not have a plane surface area with a normal that is parallel and opposite to the general conveying direction.

7. The process of claim 1, wherein at least one mixing element does not have a face that is perpendicular to the general conveying direction.

8. The process of claim 1, wherein at least one mixing element does not have abutting faces that are perpendicular to the general conveying direction.

9. The process of claim 1, wherein at least part of the matrix-forming agent is fed to a hopper of the extruder and at least one component selected from
   (i) the remainder of the matrix-forming agent,
   (ii) an active ingredient,
   (iii) an additive, and
   (iv) combinations thereof,
   is introduced into the extruder through an opening in the extruder barrel at a position upstream of or in a mixing section or reverse-flight section.

10. The process of claim 9, wherein the at least one component is introduced into the extruder at a position at or close to the junction of the feeding and conveying section and a mixing section or reverse-flight section.

11. The process of claim 9, wherein the at least one component is liquid or liquefied.

12. The process of claim 9, wherein the at least one component comprises a pharmaceutically acceptable surfactant.

13. The process of claim 1, wherein the pharmaceutical active ingredient is dispersed in a polymer in a state of a solid solution.

14. The process of claim 1, wherein the matrix-forming agent comprises a pharmaceutically acceptable polymer.

15. The process of claim 14, wherein the pharmaceutically acceptable polymer is selected from the group consisting of homopolymers of N-vinyl lactams, copolymers of a N-vinyl lactam and one or more comonomers selected from nitrogen-containing monomers and oxygen-containing monomers, cellulose esters and cellulose ethers, high molecular poly-alkylene oxides, polyacrylates and polymethacrylates, oligo- and polysaccharides, poly(hydroxy acids), or mixtures thereof.

16. The process of claim 1, wherein the matrix-forming agent comprises a member selected from polyols, waxes and lipids.

17. The process of claim 1, additionally comprising feeding at least one additive selected from the group consisting of flow regulators, lubricants, fillers, disintegrants, plasticizers, stabilizers or preservatives into the extruder.

18. The process of claim 1, wherein the extrudate is directly shaped into a dosage form.

19. The process of claim 18, wherein shaping is carried out by calendaring, injection moulding or profile extrusion.

20. The process of claim 1, additionally comprising grinding the solidified extrudate.

21. The process of claim 20, additionally comprising compressing said solid dispersion product into a tablet or filling said solid dispersion product into a capsule shell.

22. The process of claim 21, additionally comprising applying a film-coat to the tablet.

23. The process of claim 1, wherein the extruder further comprises a barrel having several heating zones, wherein the portion of the barrel upstream of the first reverse-flight element is maintained at a lower temperature than the portion of the barrel downstream of the first reverse-flight element.

24. The process of claim 1, wherein the processing elements defining the reverse-flight section comprise at least two reverse-flight elements and at least one positive-flight screw-type element which is arranged between said two reverse-flight elements.

25. The process of claim 24, wherein said at least two reverse-flight elements have a screw pitch ranging from −0.5 times to −1.5 times the screw pitch of the at least one positive-flight screw-type element arranged between the at least two reverse-flight elements.

26. The process of claim 24, wherein the said at least two reverse-flight elements have a screw pitch ranging from −0.5 time to −1.5 times the screw pitch of the at least one positive flight screw-type element arranged between the at least two reverse-flight elements.

27. The process of claim 1, wherein the amount of degradation of the active ingredient relative to the amount of active ingredient is less than 0.381%.

28. A process for producing a solid dispersion of a pharmaceutical active ingredient which comprises feeding the pharmaceutical active ingredient and a matrix-forming agent to an extruder and forming a uniform extrudate, wherein at least 98% by weight of the total amount of active ingredient is present in an amorphous state and wherein the amount of degradation of the active ingredient relative to the amount of active ingredient is less than 0.381%;

wherein the extruder comprises a housing, and at least two rotating shafts within said housing, wherein each of the shafts carries a plurality of processing elements disposed axially one behind the other, the processing elements defining
(i) a feeding and conveying section,
(ii) a first mixing section,
(iii) an intermediate conveying section,
(iv) a reverse-flight section, and
(v) a discharging section, wherein the processing elements defining the first mixing section comprise at least one mixing element and the processing elements defining the reverse-flight section comprise at least one mixing element and downstream thereto at least one reverse-flight element, wherein the at least one reverse-flight element is based on a screw-type element having a conveying direction opposite to the general conveying direction of the extruder;

wherein at least one mixing element is derived from a screw-type element, has recesses formed in the screw-flight of the screw-type element, and has a plurality of concentric ring portions formed by grooves turned into the screw-type element; and wherein the processing elements are sized and configured to provide a recurring sequence of pressure build-up that forces the pharmaceutical active ingredient through an annular gap between the extruder housing and ring portions of the mixing element with shearing action and elongation, followed by a reduction in pressure, thereby causing a defined and uniform but not undue stress on the pharmaceutical active ingredient, thereby avoiding high temperatures or high local shear forces that cause decomposition of the pharmaceutical active ingredient and preventing residues of extruded material from remaining within the extruder over extended periods of time; and wherein said mixing elements enable a sufficient degree of mixing or homogenization with less degradation of the active ingredient or formation of other ingredients as compared to degradation of the active ingredient or formation of other ingredients resulting from a process employing paddle means or mixing blocks.

* * * * *